US008981771B2

(12) United States Patent
Thompson et al.

(10) Patent No.: US 8,981,771 B2
(45) Date of Patent: Mar. 17, 2015

(54) AIRCRAFT FUSELAGE INSPECTION SYSTEM

(75) Inventors: Jeffrey G. Thompson, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 632 days.

(21) Appl. No.: 13/152,475

(22) Filed: Jun. 3, 2011

(65) Prior Publication Data

US 2012/0306482 A1 Dec. 6, 2012

(51) Int. Cl.
*G01N 22/02* (2006.01)
*B64F 5/00* (2006.01)

(52) U.S. Cl.
CPC ............. *G01N 22/02* (2013.01); *B64F 5/0045* (2013.01)
USPC ............ 324/240; 324/238; 324/242; 324/232

(58) Field of Classification Search
CPC .. G01R 31/008; G01R 31/021; G01R 31/085; G01N 27/9046; G01N 27/82; G01N 27/904
USPC .......................... 324/637, 240, 238, 242, 232
See application file for complete search history.

(56) References Cited

U.S. PATENT DOCUMENTS

| | | | | |
|---|---|---|---|---|
| 4,864,260 A * | 9/1989 | Huard | ............................ | 333/255 |
| 6,545,469 B1 * | 4/2003 | Batzinger et al. | ............. | 324/238 |
| 7,301,335 B2 * | 11/2007 | Sun et al. | ....................... | 324/240 |
| 7,352,176 B1 * | 4/2008 | Roach et al. | ................... | 324/240 |
| 7,626,383 B1 * | 12/2009 | Sun et al. | ....................... | 324/240 |
| 8,274,279 B2 * | 9/2012 | Gies | ............................... | 324/240 |
| 2007/0069720 A1 * | 3/2007 | Goldfine et al. | .............. | 324/240 |
| 2009/0302835 A1 * | 12/2009 | Sun et al. | ....................... | 324/240 |

OTHER PUBLICATIONS

Ghasr et al. Millimeter-Wave Differential Probe for Nondestructive Detection of Corrosion Precursor Pitting, IEEE vol. 55, No. 5, Oct. 2006, pp. 1620-1627.*
Zoughi et al., "Microwave and millimetre wave sensors for crack detection", 2008, Fatigue & Fracture Engineering Materials & Structures, vol. 31, No. 8 pp. 695-713.
Wang et al., "Interaction of Surface Cracks in Metals with Open Ended Coaxial Probes at Microwave Frequencies", Aug. 2000, Materiaols Evaluation, vol. 58, No. 10, pp. 1228-1234, Oct. 2000.
Ghasr et al., "Millimeter-Wave Differential Probe for Nondestructive Detection of Corrosion Precursor Pitting", IEEE Transactions on Instrumentation and Measurement, vol. 55, No. 5, Oct. 2006, pp. 1620-1627.

* cited by examiner

*Primary Examiner* — Tung X Nguyen
*Assistant Examiner* — Alesa Allgood
(74) *Attorney, Agent, or Firm* — Yee & Associates, P.C.

(57) ABSTRACT

A method and apparatus for inspecting a metallic structure. A first signal is sent into a first location in the metallic structure and a second signal into a second location in the metallic structure at substantially a same time. A first response to the first signal is received. A second response to the second signal is received. The first response is compared with the second response to form a comparison. A determination is made as to whether an inconsistency is present using the comparison.

20 Claims, 10 Drawing Sheets

AIRCRAFT FUSELAGE INSPECTION SYSTEM

BACKGROUND INFORMATION

1. Field

The present disclosure relates generally to aircraft and, in particular, to inspecting aircraft. Still more particularly, the present disclosure relates to a method and apparatus for identifying inconsistencies in the fuselage of an aircraft.

2. Background

An aircraft undergoes stresses each time a flight occurs. Stress occurs on the aircraft from the forces that occur during takeoff and landing. Some of the stresses occur from forces of the aircraft landing on the runway. Other stresses that occur during takeoff and landing involve the pressurization of the aircraft. The pressurization and depressurization of the aircraft cause the metal skin of an aircraft to expand and contract.

This change in the aircraft results in the bending of the frame and the skin of the aircraft. Over time, this bending may cause inconsistencies to form, grow, or both. These inconsistencies are often not visible to the naked eye.

Airlines often perform maintenance to identify these inconsistencies. This maintenance is often governed by regulations set by regulatory agencies, such as the Federal Aviation Administration (FAA).

Part of this maintenance involves a detailed inspection of the aircraft. When inconsistencies are found, maintenance in the form of rework may be performed to reduce inconsistencies.

Some inspections may require disassembly of the aircraft. This disassembly may allow inspectors to look at areas that are normally not visible. Additionally, non-destructive testing, such as eddy current testing, also may be performed on the aircraft. Eddy current testing may be used to identify inconsistencies that may not be visible to the naked eye.

In some cases, paint may be removed to perform some of the inspections. Some paints or coatings have a conductive material that may make it more difficult to identify inconsistencies when eddy current testing is used. Eddy current testing uses electromagnetic induction to identify inconsistencies in conductive materials, such as metal skin panels.

These types of inspections may require more time and expense than desired. For example, the disassembly of an aircraft results in the aircraft being out of service and unable to generate revenues for the airline.

Therefore, it would be advantageous to have a method and apparatus that takes into account at least some of the issues discussed above, as well as possibly other issues.

SUMMARY

In one advantageous embodiment, a method for inspecting a metallic structure is provided. A first signal is sent into a first location in the metallic structure and a second signal into a second location in the metallic structure at substantially a same time. A first response to the first signal is received. A second response to the second signal is received. The first response is compared with the second response to form a comparison. A determination is made as to whether an inconsistency is present using the comparison.

In another advantageous embodiment, a method for inspecting a metallic skin on an aircraft is provided. A first polarized signal is sent from a first waveguide into a first location in the metallic skin on a first side of a fastener and a second polarized signal from a second waveguide into a second location in the metallic skin on a second side of the fastener at substantially a same time. A first response to the first polarized signal is received. A second response to the second polarized signal is received. The first response is subtracted from the second response to form a comparison. A determination is made as to whether an inconsistency is present using the comparison.

In yet another advantageous embodiment, an apparatus comprises a first waveguide, a second waveguide, and a signal analyzer. The first waveguide is configured to send a first signal into a first location in a metallic structure. The first waveguide is further configured to receive a first reply to the first signal. The second waveguide is configured to send a second signal into a second location in the metallic structure in which the first signal and the second signal are sent at substantially a same time. The first signal is configured to receive a second reply to the second signal. The signal analyzer is connected to the first waveguide and the second waveguide. The signal analyzer is configured to receive a first response from the first waveguide, receive a second response from the second waveguide, and compare the first response with the second response to form a comparison. The comparison is used to determine whether an inconsistency is present.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
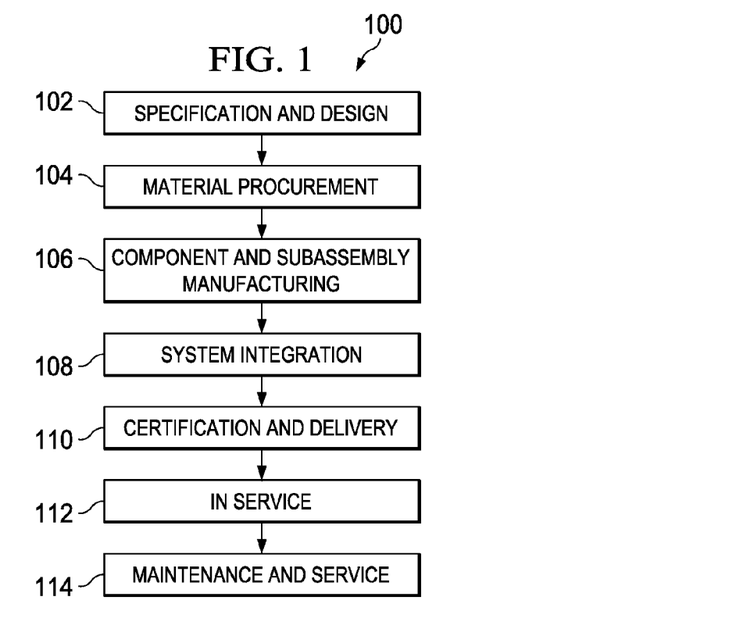
FIG. 1 is an illustration of an aircraft manufacturing and service method in accordance with an advantageous embodiment.
Figure 2:
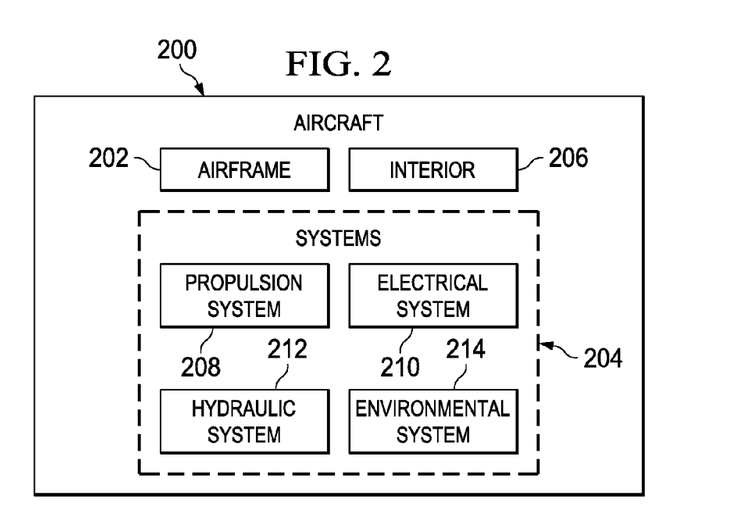
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. In particular, one or more of the different advantageous embodiments may be used to perform inspection of aircraft 200 during component and subassembly manufacturing, maintenance and service 114, and other phases of the aircraft manufacturing and service method.

The different advantageous embodiments recognize and take into account a number of considerations. For example, the different advantageous embodiments recognize and take into account that eddy current testing may have limitations with respect to inconsistencies located around fasteners in the skin panels used to form the fuselage of an aircraft. The different advantageous embodiments recognize and take into account that difficulty in identifying inconsistencies located around fasteners may occur from a use of a different type of metal in the fastener, as compared to the type of metal in the skin panel. In particular, eddy current testing near features, such as fasteners, is affected by the electrical conductivity differences between the structure and the fastener. This difference may limit the sensitivity of this type of testing to detect inconsistencies.

The different advantageous embodiments also recognize and take into account that identifying inconsistencies in aluminum skin panels used in fuselages may be more difficult than desired using eddy current systems. The different advantageous embodiments recognize and take into account that current eddy current systems may not identify inconsistencies until they extend about 0.10 inches or greater in length from the head of the fastener. The different advantageous embodiments recognize and take into account that with this situation, more frequent inspections may be needed than desired.

Therefore, the different advantageous embodiments provide a method and apparatus for inspecting an aircraft. A first signal is sent into a first location in a metallic skin, and a second signal is sent into a second location in the metallic structure. These two signals are sent into the metallic structure at the two locations at substantially the same time. A first response is received to the first signal, and a second response is received to the second signal. The first response is compared with the second response to form a comparison. A determination is made as to whether an inconsistency is present using this comparison.

Figure 3:
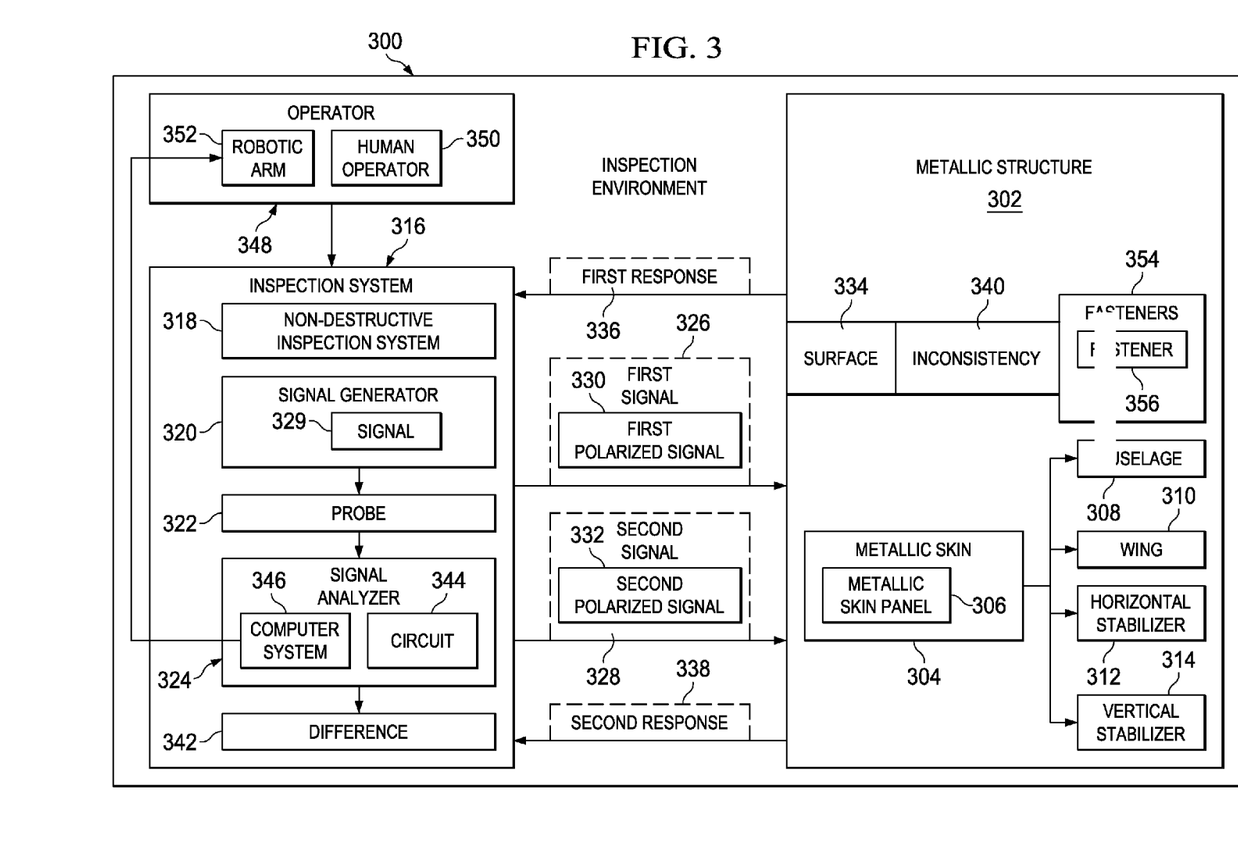
FIG. 3 is an illustration of an inspection environment in accordance with an advantageous embodiment.

With reference now to FIG. 3, an illustration of an inspection environment is depicted in accordance with an advantageous embodiment. Inspection environment 300 is an example of an inspection environment in which different parts of aircraft 200 in FIG. 2 may be inspected.

In one illustrative example, an inspection of metallic structure 302 may be made. Metallic structure 302 may be any metallic structure within aircraft 200 in FIG. 2. In these illustrative examples, a metallic structure is any structure that has characteristics of a metal. In other words, a metallic structure may be formed of metal or may be a metallic compound.

In these illustrative examples, metallic structure 302 may be, in particular, metallic skin 304. Metallic skin 304 may be metallic skin panel 306 for fuselage 308, wing 310, horizontal stabilizer 312, vertical stabilizer 314, and/or other structures that may be present in aircraft 200 in FIG. 2.

For example, metallic skin 304 may be selected from one of a skin panel, an engine housing, a fan blade, or some other suitable structure present in aircraft 200. In some illustrative examples, metallic skin 304 may be selected from one of aircraft 200 in FIG. 2, a submarine, a spacecraft, a surface ship, an automobile, a bridge, a building, and/or some other suitable structure.

In these illustrative examples, the inspection of metallic structure 302 may be performed using inspection system 316. Inspection system 316 takes the form of non-destructive inspection system 318.

In these illustrative examples, inspection system 316 comprises signal generator 320, probe 322, and signal analyzer 324. Signal generator 320 is configured to generate first signal 326 and second signal 328. In these illustrative examples, first signal 326 and second signal 328 may have frequencies selected from different ranges. For example, millimeter waves may be used for first signal 326 and second signal 328. Millimeter waves may have a frequency from about 30 gigahertz to about 300 gigahertz. These waves may have a wavelength from about one millimeter to about 10 millimeters, depending on the particular implementation.

First signal 326 and second signal 328 are sent through probe 322 into metallic structure 302 in these illustrative examples. As depicted, probe 322 is configured to polarize first signal 326 and second signal 328. In other words, first signal 326 may be first polarized signal 330, and second signal 328 may be second polarized signal 332 when those signals are emitted from probe 322.

In these illustrative examples, probe 322 may be in contact with surface 334 of metallic structure 302 when first signal 326 and second signal 328 are sent into metallic structure 302. First response 336 is received by probe 322 in response to first signal 326. Second response 338 is received in response to second signal 328 by probe 322. Although probe 322 is described as being in contact with surface 334, probe 322 does not need to actually contact surface 334. Probe 322 only needs to be close enough to surface 334 to obtain a desired quality for first response 336 and second response 338.

In these illustrative examples, first response 336 and second response 338 are analyzed to determine whether inconsistency 340 is present in metallic structure 302. In one illustrative example, probe 322 may generate difference 342. Probe 322 may take the difference between first response 336 and second response 338. Difference 342 may then be sent to signal analyzer 324 for analysis.

In another illustrative example, signal analyzer 324 receives first response 336 and second response 338. In these illustrative examples, signal analyzer 324 subtracts first response 336 from second response 338 to identify difference 342 between first response 336 and second response 338.

Based on difference 342, signal analyzer 324 makes a determination as to whether inconsistency 340 is present. In these illustrative examples, signal analyzer 324 may take different forms. For example, signal analyzer 324 may be circuit 344, computer system 346, or some other suitable component. In these illustrative examples, non-destructive inspection system 318 is operated by operator 348, which may move probe 322 over different portions of surface 334 of metallic structure 302. Operator 348 may be, for example, human operator 350, robotic arm 352 controlled by computer system 346, or some other suitable type of operator.

In these illustrative examples, inspection system 316 may be especially useful when fasteners 354 are present in metallic structure 302. Oftentimes, fasteners 354 may have a different material from metallic structure 302. As a result, currently used eddy current testing systems may not detect inconsistency 340 as early as desired when inconsistency 340 extends or grows from fastener 356 in fasteners 354.

In these illustrative examples, inspection system 316 may be especially useful for detecting inconsistency 340 when inconsistency 340 takes the form of a crack that extends from or near fasteners 354. Inspection system 316 provides an improvement over currently used eddy current inspection system techniques. Inspection system 316 may have a greater sensitivity in detecting inconsistency 340 near or extending from fasteners 354.

In these illustrative examples, signal generator 320 may be implemented using one oscillator, two oscillators, or some other suitable circuit configured to generate first signal 326 and second signal 328. For example, signal generator 320 may comprise a signal oscillator that generates signal 329. Signal 329 may then be split into first signal 326 and second signal 328.

As another example, the splitting of signal 329 may occur in signal generator 320 or in probe 322. If the signal splitting occurs in probe 322, then signal generator 320 is still considered to have generated first signal 326 and second signal 328 but indirectly by signal 329 being split in probe 322. In other words, signal generator 320 may directly or indirectly generate first signal 326 and second signal 328 in these illustrative examples.

Figure 4:
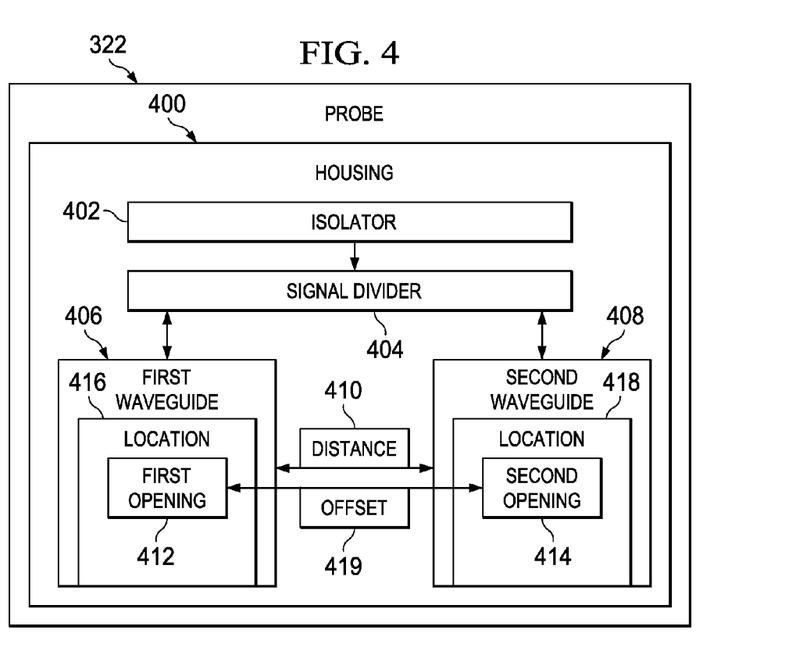
FIG. 4 is an illustration of a block diagram of a probe in accordance with an advantageous embodiment.

With reference now to FIG. 4, an illustration of a block diagram of a probe is depicted in accordance with an advantageous embodiment. In this illustrative example, example components for probe 322 are depicted in accordance with an advantageous embodiment.

As illustrated, probe 322 comprises housing 400, isolator 402, signal divider 404, first waveguide 406, and second waveguide 408. In these illustrative examples, housing 400 may comprise a structure for which other components are connected to or held. Isolator 402 is connected to signal divider 404. Signal divider 404 has outputs connected to first waveguide 406 and second waveguide 408.

As used herein, a first component "connected to" a second component means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

Isolator 402 is configured to reduce unwanted reflections that may result from signal divider 404 receiving a signal from signal generator 320 in FIG. 3. In these illustrative examples, signal divider 404 receives signal 329 from signal generator 320 to generate first signal 326 and second signal 328. Isolator 402 reduces undesired reflections from signal divider 404 returning to signal generator 320.

In these illustrative examples, signal divider 404 divides the signal generated by signal analyzer 324 to form first signal 326 and second signal 328, which are sent through first waveguide 406 and second waveguide 408, respectively.

First waveguide 406 generates first polarized signal 330 from first signal 326. Second waveguide 408 generates second polarized signal 332 from second signal 328. In these illustrative examples, first waveguide 406 and second waveguide 408 are arranged parallel to each other. The size and shape of first waveguide 406 relative to first signal 326 and the shape and size of second waveguide 408 relative to second signal 328 polarizes the signals to form first polarized signal 330 and second polarized signal 332.

First waveguide 406 and second waveguide 408 may be separated from each other by distance 410. More specifically, first opening 412 in first waveguide 406 and second opening 414 in second waveguide 408 have distance 410. Distance 410 may be an adjustable distance. In these illustrative examples, distance 410 may be adjusted to allow first waveguide 406 to contact surface 344 of metallic structure 302 on one side of fastener 356 with second waveguide 408 contacting surface 334 of metallic structure 302 on the opposite side of fastener 356.

In these illustrative examples, first waveguide 406 has first opening 412 that may contact surface 334 to send first signal 326 into metallic structure 302. In a similar fashion, second waveguide 408 has second opening 414, which may be in contact with surface 334 to send second signal 328 into metallic structure 302. With respect to adjusting distance 410, first waveguide 406 and second waveguide 408 are adjusted such that first opening 412 and second opening 414 are on either side of a fastener.

In these illustrative examples, first opening 412 has location 416 in first waveguide 406, and second opening 414 has location 418 in second waveguide 408.

Location 416 and location 418 have offset 419 from each other in these illustrative examples. Offset 419 may be selected to reduce any interaction between first signal 326 and second signal 328. Further, location 416 and location 418 may be selected to also reduce interaction that may occur between first response 336 and second response 338. In other words, interaction between the signals and responses may be undesirable to obtain information needed to identify whether inconsistency 340 is present in metallic structure 302.

In these illustrative examples, first response 336 and second response 338 are received by first waveguide 406 and second waveguide 408, respectively. First response 336 and second response 338 are received as replies to first signal 326 and second signal 328, respectively. These responses are sent by signal divider 404 to signal analyzer 324 in these illustrative examples.

Signal divider 404 is also connected to signal analyzer 324. Signal divider 404 may be implemented using a magic tee. A magic tee is a currently-used structure that functions as a splitter for signals. A magic tee may also be referred to as a magic T or a hybrid tee. A magic tee is a combination of E and H plane tees. A magic tee may be used as a coupler in various microwave systems.

Further, when a magic tee is used to implement signal divider 404, signal divider 404 also may generate difference 342 from first response 336 and second response 338. In this type of implementation, signal divider 404 sends difference 342 to signal analyzer 324. Signal analyzer 324 does not generate difference 342 from first response 336 and second response 338 with this type of implementation. The magic tee is configured to combine first response 336 and second response 338 to form difference 342.

In these illustrative examples, first polarized signal 330 and second polarized signal 332 are configured to have a polarization that is substantially perpendicular to inconsistency 340. For example, when inconsistency 340 takes the form of a crack, first polarized signal 330 and second polarized signal 332 are substantially perpendicular to the crack. In other words, these signals are substantially perpendicular to a direction in which the crack extends.

In these illustrative examples, the amplitude of the wave in first signal 326 is substantially perpendicular to a plane in which inconsistency 340 is located. In other words, in these examples, it is desirable for the amplitude of the first signal and the second signal to interact with the inconsistency as much as possible if one of the signals encounters inconsistency 340 to provide a difference between first response 336 and second response 338 in a manner that may be used to identify inconsistency 340.

The illustration of inspection environment 300 in FIG. 3 and example components for probe 322 in FIG. 4 are not meant to imply physical or architectural limitations to the manner in which an advantageous embodiment may be implemented. Other components in addition to, and/or in place of, the ones illustrated may be used. Some components may be unnecessary. Also, the blocks are presented to illustrate some functional components. One or more of these blocks may be combined and/or divided into different blocks when implemented in an advantageous embodiment.

Many of these blocks represent functional components and may be implemented in many different ways in a physical form. For example, inspection system 316 is depicted as having three components: signal generator 320, probe 322, and signal analyzer 324.

Depending on the particular implementation, these different components may be implemented as a single, physical unit. For example, a housing may hold signal generator 320, probe 322 and signal analyzer 324.

In other examples, signal generator 320 and probe 322 may be manufactured as a single component that is manipulated by operator 348. The responses are sent to signal analyzer 324 in another location. The responses may be sent through a network, wireless communications links, or some other suitable fashion when inspection system 316 takes this form.

In yet other illustrative examples, probe 322 may be a separate component manipulated by operator 348 with signal generator 320 being connected to probe 322 as a separate component that is not manipulated by operator 348. These and other variations in the manner in which inspection system 316 may be implemented are contemplated by an advantageous embodiment.

As another example, in some illustrative examples, signal divider 404 may be omitted. Instead, signal analyzer 324 may include two oscillators that generate first signal 326 and second signal 328. In still another illustrative example, isolator 402 may be considered part of signal generator 320 rather than probe 322, depending on the particular implementation. Further, in some cases, signal analyzer 324 may be integrated in housing 400 with probe 322.

In yet another illustrative example, one or more additional waveguides in addition to first waveguide 406 and second waveguide 408 may be used. These additional waveguides may generate additional signals that may be used in determining whether an inconsistency is present. For example, probe 322 may have three waveguides, four waveguides, seven waveguides, or some other number of waveguides, depending on the number of signals desired to be sent into the structure and the number of responses desired for comparison. The configuration of these waveguides may be selected to provide desired responses to determine whether an inconsistency is present. The configuration may be, for example, without limitation, the spacing or offset between openings in the waveguides.

In still other illustrative examples, inspection system 316 may be applied to inspect other platforms in addition to aircraft 200 in FIG. 2. For example, the different advantageous embodiments may be employed to inspect a mobile platform, a stationary platform, a land-based structure, an aquatic-based structure, a space-based structure, and/or some other suitable type of object. More specifically, the different advantageous embodiments may be applied to, for example, without limitation, a submarine, a bus, a personnel carrier, a tank, a train, an automobile, a spacecraft, a space station, a satellite, a surface ship, a power plant, a bridge, a building, and/or some other suitable type of object.

Figure 5:
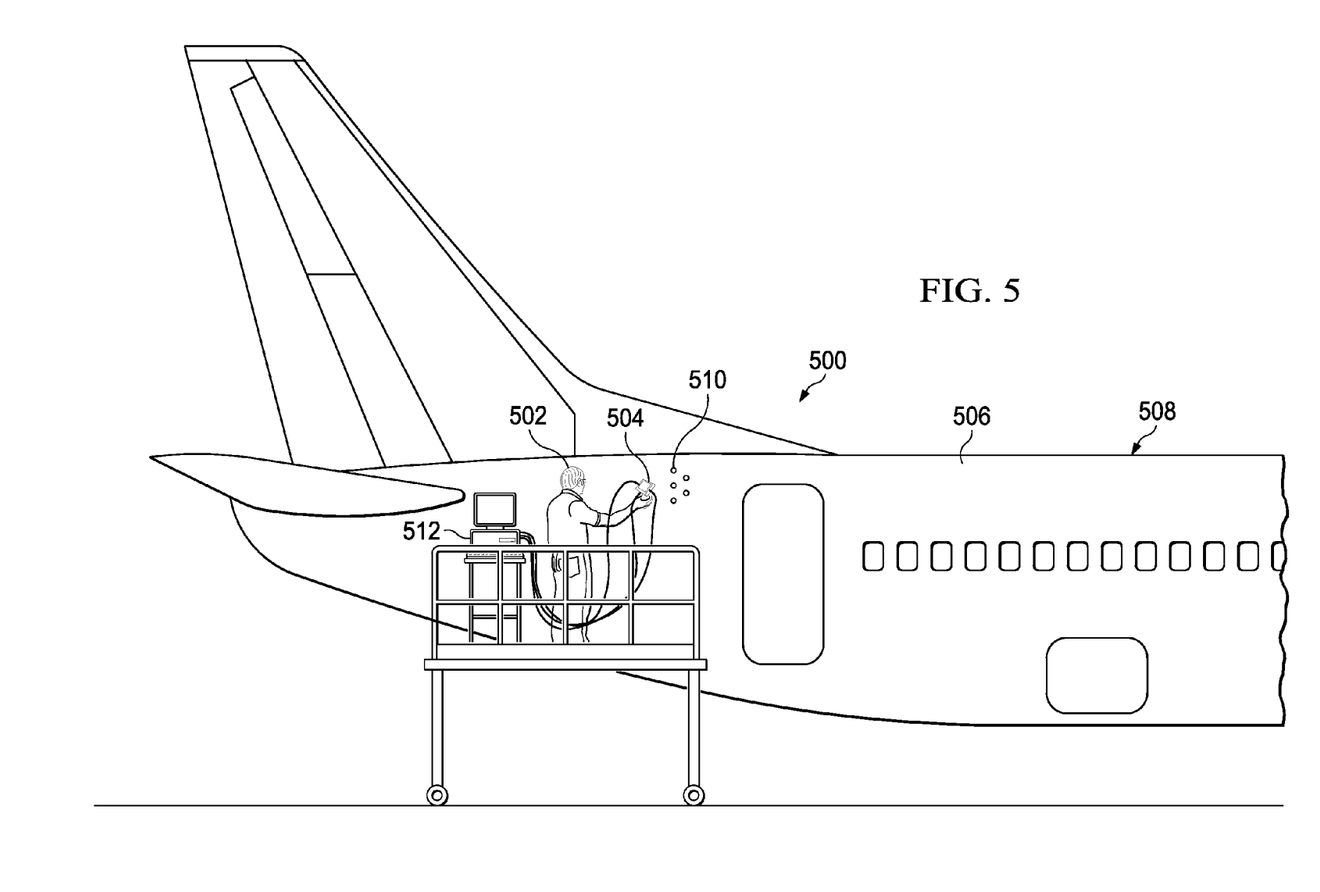
FIG. 5 is an illustration of an inspection environment in accordance with an advantageous embodiment.

With reference now to FIG. 5, an illustration of an inspection environment is depicted in accordance with an advantageous embodiment. In this illustrative example, inspection environment 500 is an example of one physical implementation of inspection environment 300 shown in block form in FIG. 3.

As depicted, operator 502 is a human operator that holds probe 504. Operator 502 moves probe 504 on metallic skin 506 for fuselage 508. Fuselage 508 is an example of a component in airframe 202 of aircraft 200 in FIG. 2 in a physical implementation. In these illustrative examples, operator 502 moves probe 504 with respect to fasteners 510 on metallic skin 506.

Responses from signals sent into metallic skin 506 are sent to computer 512 for analysis. In this illustrative example, operator 502 may move probe 504 with respect to fasteners 510 such that computer 512 may make an analysis of metallic skin 506 in these areas to determine whether an inconsistency is present. This inspection of metallic skin 506 may occur without disassembly or removal of paint from fuselage 508.

Figure 6:
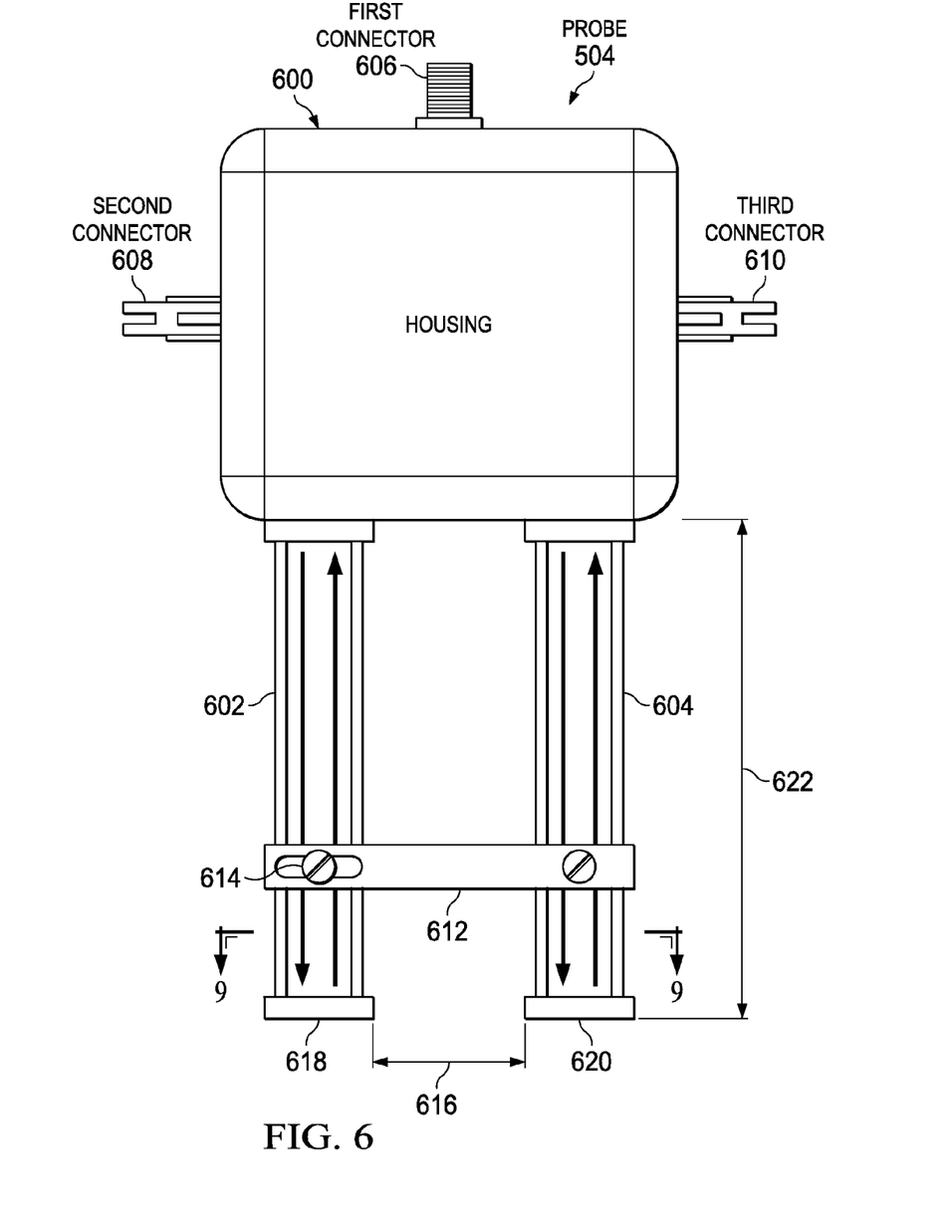
FIG. 6 is a more detailed illustration of a probe in accordance with an advantageous embodiment.

With reference now to FIG. 6, a more detailed illustration of probe 504 is depicted in accordance with an advantageous embodiment. In this illustrative example, probe 504 comprises housing 600 to which first waveguide 602 and second waveguide 604 are adjustably connected. Probe 504 has first connector 606, which is configured for connection to signal generator 320 in FIG. 3. Probe 504 also has second connector 608 and third connector 610. These two connectors are configured for connection to signal analyzer 324 in FIG. 3.

Bar 612 is connected to first waveguide 602 and second waveguide 604. Adjusting screw 614 is present, which may be used to secure first waveguide 602 to bar 612 when distance 616 between first waveguide 602 and second waveguide 604 has been selected. Distance 616 may be selected such that openings (not shown) at end 618 of first waveguide 602 and end 620 at second waveguide 604 within these waveguides may sit on either side of a fastener, such as a fastener in fasteners 510 in FIG. 5.

In this illustrative example, first waveguide 602 and second waveguide 604 have length 622. Length 622 may be about 2 inches in this particular example. Length 622 may have a range from about 1 inch to about 4 inches.

Figure 7:
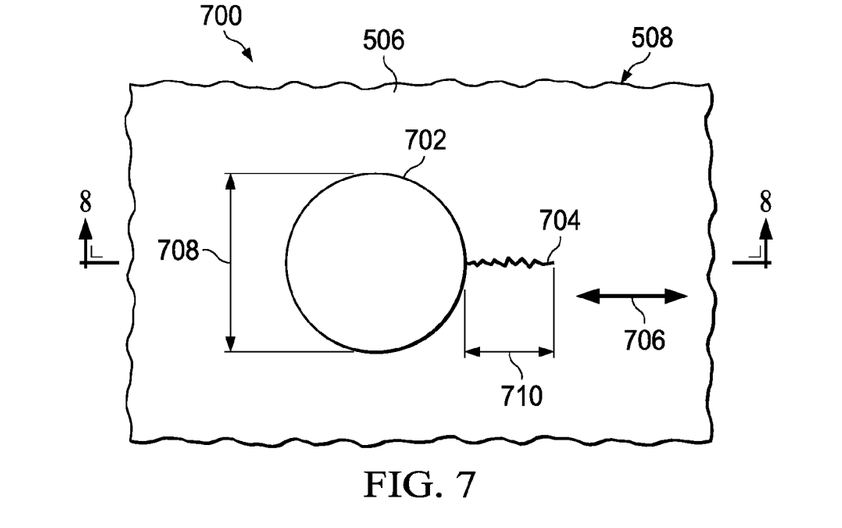
FIG. 7 is an illustration of an inconsistency in a metallic skin panel in accordance with an advantageous embodiment.

With reference now to FIG. 7, an illustration of an inconsistency in a metallic skin panel is depicted in accordance with an advantageous embodiment. In this illustrative example, fastener 702 in fasteners 510 are illustrated in metallic skin 506. Further, inconsistency 704 is present in this illustrative example. Inconsistency 704 extends in a direction indicated by arrow 706. Arrow 706 extends through a fuselage on which skin panel 700 is located. Arrow 706 extends in a direction that is longitudinal with respect to fuselage 508 in these illustrative examples.

In these illustrative examples, inconsistencies, such as inconsistency 704, typically extend in the direction of arrow 706 based on the stresses and construction of the fuselage of aircraft 200 in FIG. 2.

In this illustrative example, fastener 702 has diameter 708. Diameter 708 is the diameter of the fastener head in these examples. Diameter 708 may vary, depending on the particular implementation. For example, when fastener 702 is used in metallic skin 506 for an aircraft, diameter 708 may be from about 0.245 inches to about 0.425 inches. Of course, other diameters may be present, depending on the use and type of fastener used to implement fastener 702.

In this illustrative example, inconsistency 704 has length 710. If length 710 is less than about 0.10 inches, then currently used techniques may not be able to identify inconsistency 704. This type of inconsistency may be identified using inspection system 316 in these illustrative examples.

Figure 8:
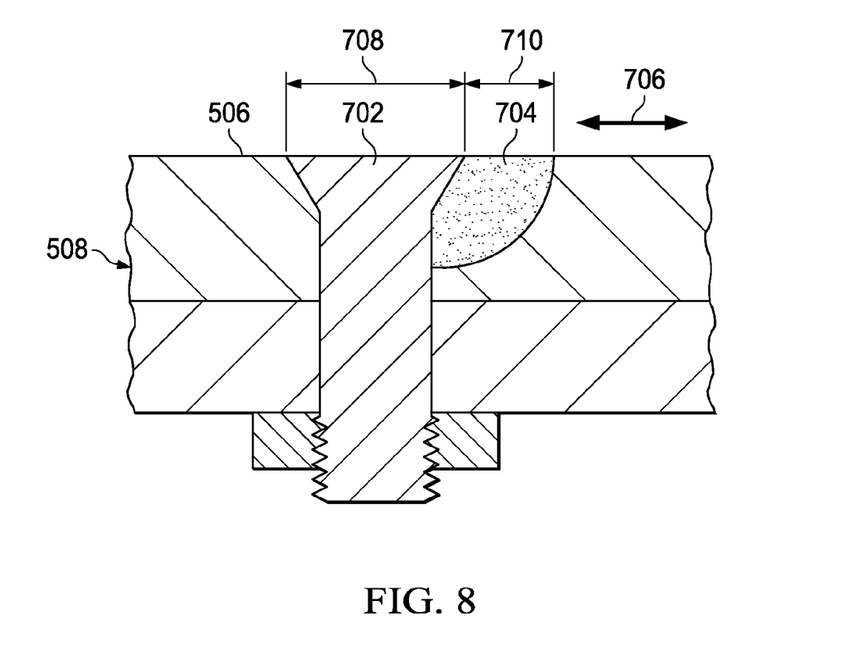
FIG. 8 is an illustration of a cross-sectional side view of a fastener with an inconsistency in a metallic skin in accordance with an advantageous embodiment.

With reference now to FIG. 8, an illustration of a cross-sectional side view of a fastener with an inconsistency in a metallic skin is depicted in accordance with an advantageous embodiment. In this illustrative example, a cross-sectional side view of fastener 702 and inconsistency 704 are illustrated.

Figure 9:
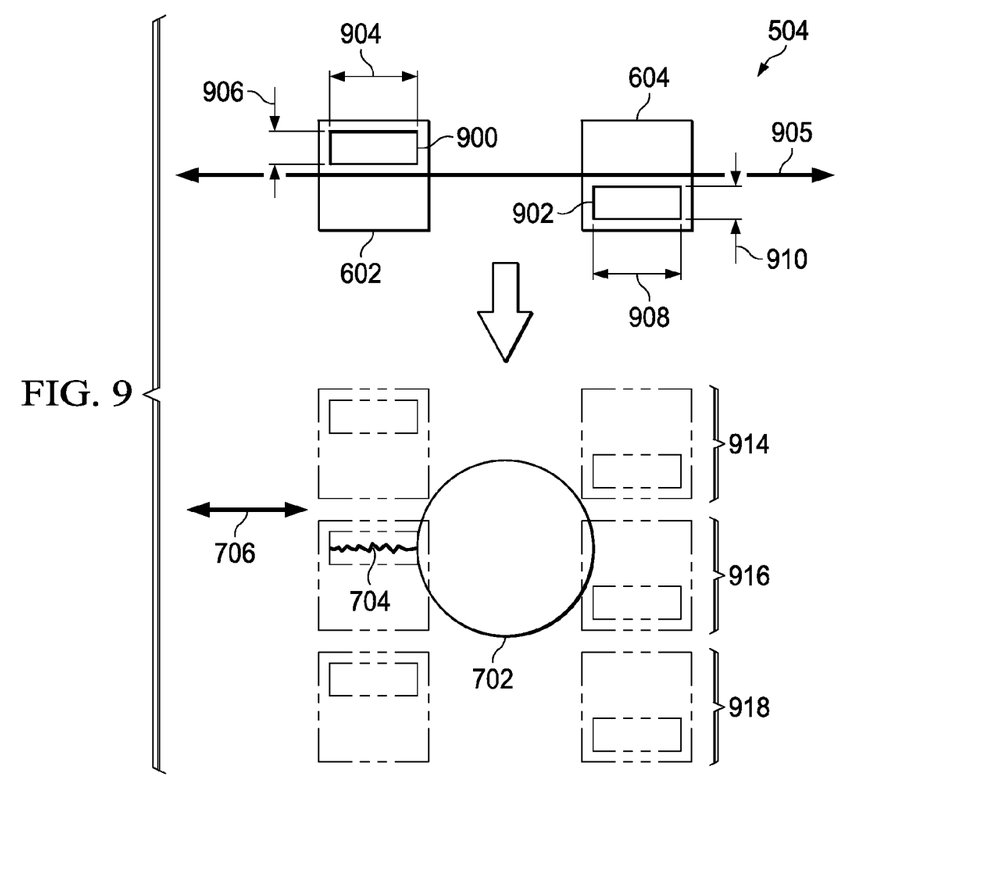
FIG. 9 is an illustration of movement of a probe over a fastener in accordance with an advantageous embodiment.

With reference now to FIG. 9, an illustration of movement of a probe over a fastener is depicted in accordance with an advantageous embodiment. In this illustrative example, a cross-sectional view of probe 504 taken along lines 9-9 in FIG. 6 is depicted in accordance with an advantageous embodiment. In this illustrative example, opening 900 in first waveguide 602 is offset from opening 902 in second waveguide 604. This offset is with respect to line 905. As discussed above, this offset may reduce a possibility of signals and/or responses interfering with each other and indicating an inconsistency is absent if an inconsistency is present on both sides of fastener 702.

In this illustrative example, opening 900 has length 904 and width 906. Opening 902 has length 908 and width 910. In these illustrative examples, length 904 and length 908 may be about 0.1 inches. Width 906 and width 910 may be about 0.05 inches.

This configuration for opening 900 and opening 902 may be used with signals having a frequency of about 94 gigahertz. These openings may be used with signals having a range from about 0.3 gigahertz to about 1100 gigahertz. The dimensions in opening 900 and opening 902 may change to provide a frequency for the signals.

Also, in the depicted examples, the waveguides have a rectangular shaped cavity as seen by opening 900 in first waveguide 602 and opening 902 in second waveguide 604. Other shapes may be used for these waveguides. For example, the shape may be circular, coaxial, double-ridged, hexagonal, octagonal, and other suitable shapes. A double-ridged shape may be a rectangular waveguide that has two ridges extending into the interior of each waveguide towards each other from opposing locations. These locations may be on the walls having a longer length.

As illustrated, probe 504 may be moved in the direction of arrow 706 with respect to fastener 702. First waveguide 602 and second waveguide 604 with openings 900 and 902 are shown in phantom in positions 914, 916, and 918. In this illustrative example, inconsistency 704 is present near fastener 702.

Figure 10:
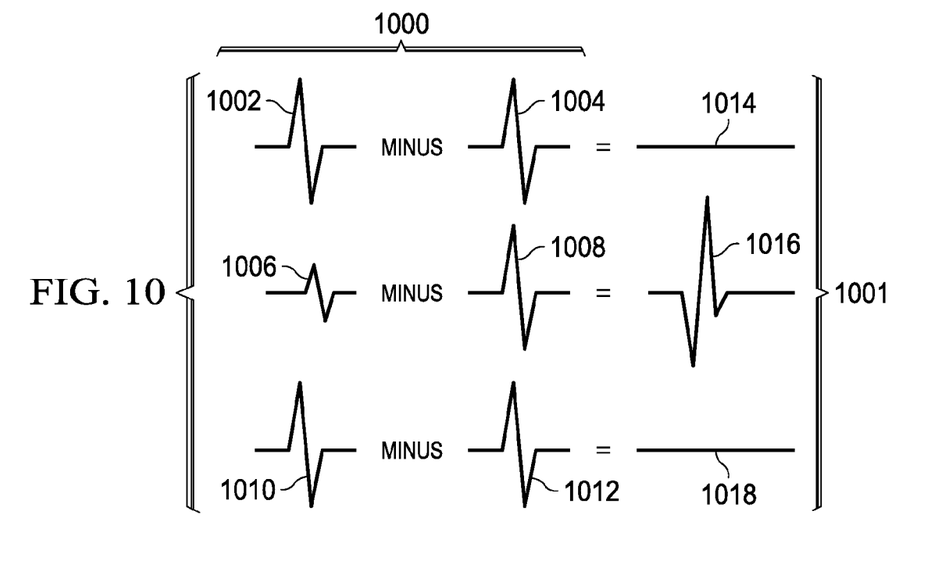
FIG. 10 is an illustration of signals and their differences in accordance with an advantageous embodiment.

With reference now to FIG. 10, an illustration of signals and their differences are depicted in accordance with an advantageous embodiment. In this illustrative example, responses 1000 in signals 1001 are examples of responses detected by first waveguide 602 and second waveguide 604 in positions 914, 916, and 918.

In this illustrative example, response 1002 is detected by first waveguide 602, and response 1004 is detected by second waveguide 604 in position 914. Response 1006 is detected by first waveguide 602, and response 1008 is detected by second waveguide 604 in position 916. Response 1010 is detected by first waveguide 602, and response 1012 is detected by second waveguide 604 in position 918.

Difference 1014 is substantially zero between response 1002 and response 1004. Difference 1014 indicates that an inconsistency is absent. Different 1016 is the difference between response 1006 and response 1008. Difference 1016 indicates that inconsistency 704 was detected when probe 504 was at position 916. Difference 1018 is the difference between response 1010 and response 1012. Difference 1018 indicates that an inconsistency was absent at position 918 in these illustrative examples.

Thus, as probe 504 is moved relative to fastener 702, an inconsistency on either side may return a difference between the responses that is not substantially zero. These differences may be measured in terms of amplitude, phase, or a combination of the two. The offset in the openings may reduce a possibility that the difference is zero if an inconsistency is present on either side of the fastener in a substantially same size and orientation.

Figure 11:
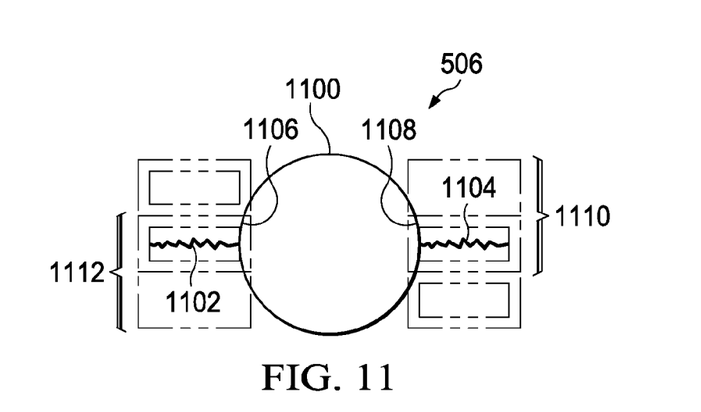
FIG. 11 is an illustration of a structure with two inconsistencies in accordance with an advantageous embodiment.

With reference now to FIG. 11, an illustration of a structure with two inconsistencies is depicted in accordance with an advantageous embodiment. In this illustrative example, metallic skin 506 has fastener 1100. Inconsistency 1102 and inconsistency 1104 are present on side 1106 and side 1108, respectively on fastener 1100. Inconsistency 1102 and inconsistency 1104 both have similar dimensions and orientations. In this illustrative example, the offset between the openings and the waveguides may prevent responses from indicating an absence of inconsistency 1102 and inconsistency 1104. As can be seen in position 1110, inconsistency 1104 may be detected. In position 1112, inconsistency 1102 may be identified.

The illustration of probe 504 and the different inconsistencies on a metallic skin panel in FIGS. 5-11 are not meant to imply physical or architectural limitations to the manner in which probe 504 may be implemented. Further, the manner in which probe 504 may be moved with respect to metallic skin 506 may be performed in different ways other than that shown. For example, probe 504 may be rotated around each fastener, rather than moved in the direction of arrow 706.

Figure 12:
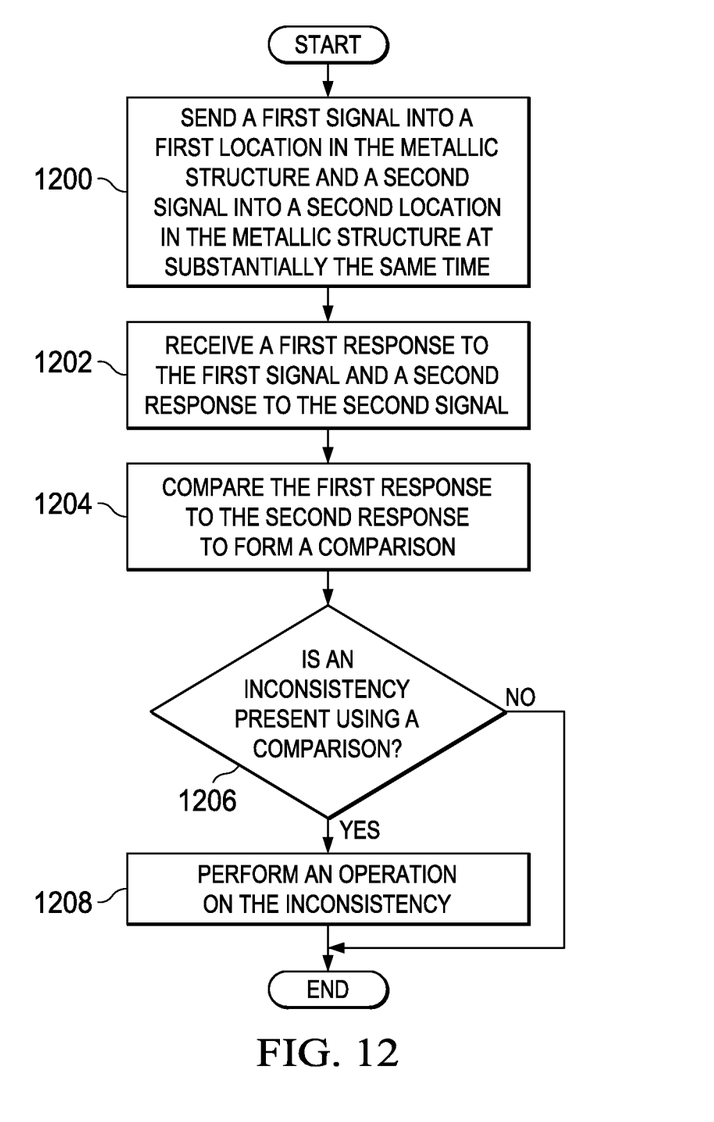
FIG. 12 is an illustration of a flowchart of a process for inspecting a structure in accordance with an advantageous embodiment.

With reference now to FIG. 12, an illustration of a flowchart of a process for inspecting a structure is depicted in accordance with an advantageous embodiment. This process may be implemented in inspection environment 300 in FIG. 3. In particular, the process may be implemented using inspection system 316 in FIG. 3.

The process begins by sending a first signal into a first location in the metallic structure and a second signal into a second location in the metallic structure at substantially the same time (operation 1200). The process receives a first response to the first signal and a second response to the second signal (operation 1202). The first response is compared to the second response to form a comparison (operation 1204).

A determination is made as to whether an inconsistency is present using a comparison (operation 1206). If an inconsistency is not present, the process terminates. Otherwise, an operation is performed on the inconsistency (operation 1208). The operation may be, for example, a rework operation. The rework operation may include reworking the metallic structure to reduce the inconsistency or replacing the metallic structure. The process terminates thereafter.

Figure 13:
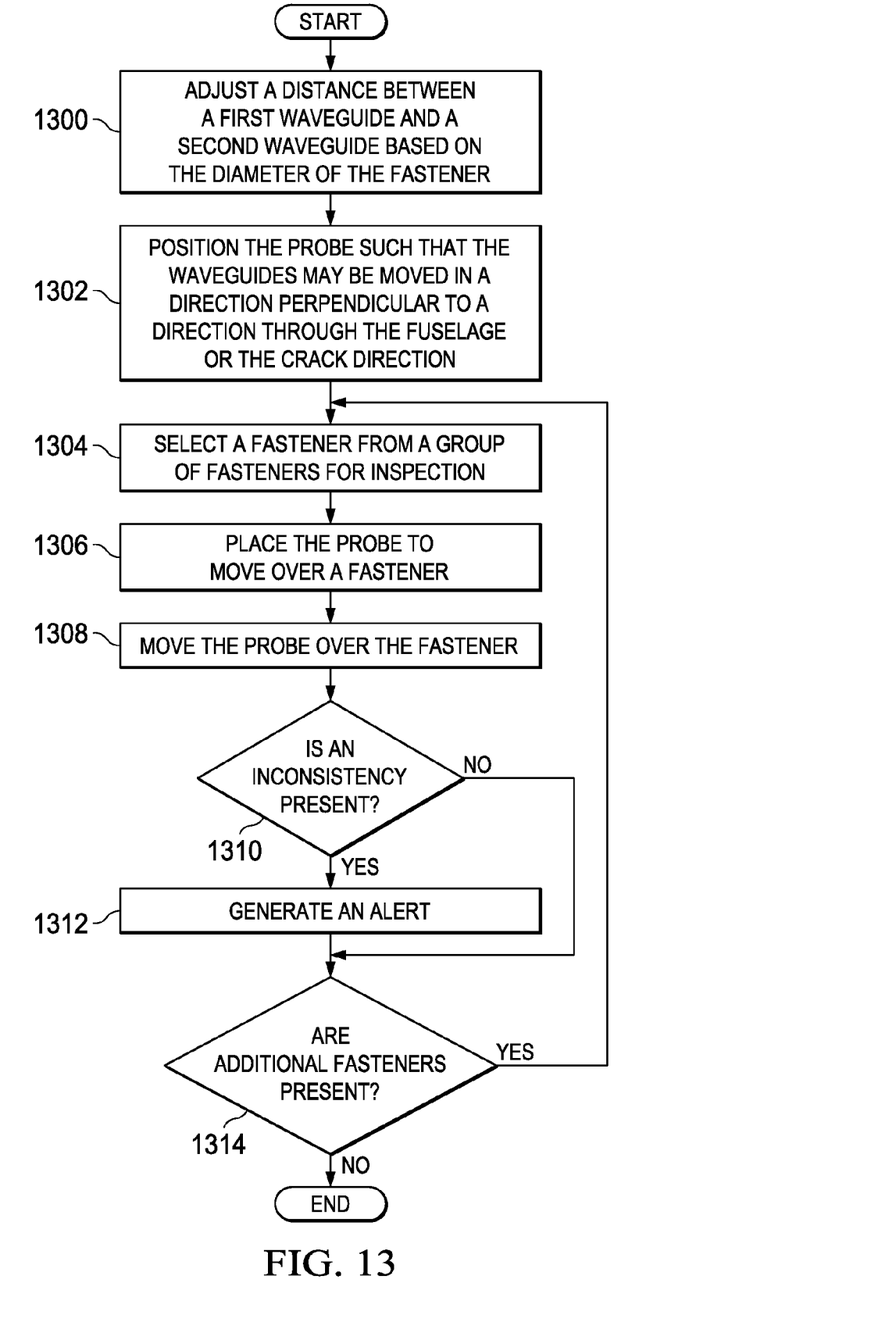
FIG. 13 is an illustration of a flowchart of a process for inspecting a metallic structure on an aircraft with fasteners in accordance with an advantageous embodiment.

With reference now to FIG. 13, an illustration of a flowchart of a process for inspecting a metallic structure on an aircraft with fasteners is depicted in accordance with an advantageous embodiment. This process may be implemented using inspection system 316 in FIG. 3.

The process begins by adjusting a distance between a first waveguide and a second waveguide based on the diameter of the fastener (operation 1300). The distance between the waveguides may be adjusted to be substantially equal to the diameter of the head of the fastener. The process then positions the probe such that the waveguide may be moved in a direction perpendicular to a direction through the fuselage or the crack direction (operation 1302). This direction perpendicular through the fuselage is from one end of the fuselage to the other end of the fuselage in these illustrative examples. In some cases, the direction of the crack may not extend or run in a direction through the fuselage.

The process then selects a fastener from a group of fasteners for inspection (operation 1304). The process places the probe to move over a fastener (operation 1306). In other words, the fastener may be located between the first waveguide and the second waveguide as the probe is moved. The process then moves the probe over the fastener (operation 1308). The probe may be moved over a fastener through the control of a computer or by human operator in operation 1308.

Next, a determination is made as to whether an inconsistency is present (operation 1310). If an inconsistency is present, an alert is generated (operation 1312). The process then determines whether additional fasteners are present (operation 1314). If an additional fastener is present, the process returns to operation 1304. Otherwise, the process terminates. With reference again to operation 1310, if an inconsistency is not present, the process proceeds to operation 1314.

In this manner, inspections of structures with fasteners may be performed in a manner that identifies inconsistencies that may normally be undetected by other inspection systems, such as other eddy current systems.

The flowcharts and block diagrams in the different depicted embodiments illustrate the architecture, functionality, and operation of some possible implementations of apparatus and methods in an advantageous embodiment. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an advantageous embodiment, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

For example, although operation 1308 may move or slide the probe over a fastener in a linear direction, other types of structures may result in a different type of placement or movement of the probe. For example, if a structure has inconsistencies that extend in different directions, the probe may be rotated or moved in some other fashion rather than in a linear direction. In addition, a combination of rotating the probe and moving the probe in a linear direction may be used, depending on the type of inconsistency to be detected.

As another example, the operation may be different in FIG. 13 if the crack direction is unknown. In this case, the probe may be rotated about the centerline of a fastener. The rotation may be done by hand or by using a rotating scanner or robotic arm that rotates the probe.

Thus, the different advantageous embodiments provide a method and apparatus for inspecting structures for inconsistencies. The different advantageous embodiments send a first signal into a first location in a metallic structure and a second signal into a second location in the metallic structure at substantially a same time. A first response to the first signal and a second response to the second signal is received. A comparison of the first response is made with the second response. A determination is made as to whether an inconsistency is present using the comparison.

With this and other features of the different advantageous embodiments, identification of inconsistencies in structures may be identified more quickly than with currently used inspection systems. In particular, the different advantageous embodiments may be especially useful for identifying inconsistencies in metallic skins in the fuselages of aircraft. In particular, these skins may be aluminum fuselage skins with paint.

The different advantageous embodiments may be especially useful in detecting inconsistencies that may extend from or around fasteners in the fuselage skins. The different advantageous embodiments recognize and take into account that currently used probes are unable to identify inconsistencies until they extend about 0.1 inches from the head of the fastener. The different advantageous embodiments may provide detection of these types of inconsistencies at smaller lengths.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments.

The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for inspecting a metallic structure for an inconsistency within 0.1 inch from a head of a fastener in the metallic structure, the method comprising:
    aligning a longitudinal axis, of a first waveguide mounted on a housing, substantially parallel to a longitudinal axis of a second waveguide mounted on the housing;
    maintaining a distance, between an edge of the first waveguide and an edge of the second waveguide, substantially equal to a diameter of the head of the fastener;
    moving the housing along an axis that substantially intersects a center point of the head, the first waveguide passing the head on one side of the axis and the second waveguide passing the head on an opposite side of the axis;
    sending, from the first waveguide, a first signal into a first location in the metallic structure;
    sending, from the second waveguide, a second signal into a second location in the metallic structure at substantially a same time as the first signal is sent;
    receiving at the first waveguide a first response to the first signal and at the second waveguide a second response to the second signal;
    comparing the first response with the second response to form a comparison; and
    determining whether the inconsistency is present using the comparison.

2. The method of claim 1, wherein the comparing step comprises:
    subtracting the first response from the second response to form the comparison.

3. The method of claim 1, further comprising:
    the first waveguide sending the first signal the first location in the metallic structure;
    the second waveguide sending the second signal into the second location in the metallic structure; and
    moving the first waveguide and the second waveguide in a direction such that the fastener passes between the first waveguide and the second waveguide.

4. The method of claim 1, wherein the first location for the first signal and the second location for the second signal are offset from each other.

5. The method of claim 1, wherein the first signal is sent into the first location in the metallic structure from a first opening comprised by the first waveguide; wherein the second signal is sent into the second location in the metallic structure from a second opening comprised by the second waveguide; and offsetting the first opening from the second opening, each opening being offset substantially perpendicular to, and on opposite sides of, a line formed from a center point comprised by an end of the first waveguide to a center point comprised by an end of the second waveguide.

6. The method of claim 1 further comprising:
    responsive to the determination that the inconsistency is present, performing a rework operation of the metallic structure to reduce the inconsistency.

7. The method of claim 1, wherein the metallic structure is a metallic skin on an aircraft.

8. The method of claim 1, wherein sending the first signal and the second signal into the metallic structure comprises;
    transmitting the first signal, from the first waveguide comprised by a probe, into the metallic structure; and;
    transmitting the second signal from the second waveguide comprised by the probe into the metallic structure.

9. The method of claim 8, wherein the first signal and the second signal are both polarized in a direction that is substantially perpendicular to a plane in which the inconsistency is expected to be located.

10. A method for inspecting a metallic skin on an object for an inconsistency within 0.1 inch from a head of a fastener in the metallic skin, the method comprises:
    aligning a longitudinal axis, of a first waveguide mounted on a housing, substantially parallel to a longitudinal axis of a second waveguide mounted on the housing;
    maintaining a distance, between an edge of the first waveguide and an edge of the second waveguide to be substantially equal to a diameter of the head of the fastener;
    moving the housing along an axis that substantially intersects a center point of the head, the first waveguide passing the head on one side of the axis and the second waveguide passing the head on an opposite side of the axis;
    sending a first polarized signal from the first waveguide into a first location in the metallic skin on a first side of the fastener and a second polarized signal from the second waveguide into a second location in the metallic skin on a second side of the fastener at substantially a same time;
    receiving at the first waveguide a first response to the first polarized signal and at the second waveguide a second response to the second polarized signal;
    subtracting the first response from the second response to form a comparison; and
    determining whether the inconsistency is present using the comparison.

11. The method of claim 10, wherein the first polarized signal and the second polarized signal are polarized in a direction that is substantially perpendicular to a plane in which the inconsistency is expected to be located.

12. The method of claim 10, further comprising moving the first waveguide and the second waveguide over the fastener such that the fastener passes between the first waveguide and the second waveguide, and wherein the metallic skin is selected from one of a skin panel, an engine housing, a fan blade, an aircraft, a submarine, a spacecraft, a surface ship, an automobile, a bridge, and a building.

13. An apparatus comprising:
a housing comprising a first waveguide and a second waveguide mounted to the housing, a longitudinal axis of the first waveguide being substantially parallel to a longitudinal axis of the second waveguide;
a bar connected to the first waveguide and the second waveguide, the bar comprising an adjustment device that adjusts a separation between the first waveguide and the second waveguide such that when the housing moves, along an axis passing through a center point of a head of a fastener in a metallic structure, the first waveguide passes the head on one side of the axis as it sends a first signal into a first location in the metallic structure and receives a first reply to the first signal, and the second waveguide passes on an opposite side of the axis as it sends a second signal into a second location in the metallic structure and receives a second reply to the second signal, the first signal and the second signal being sent substantially simultaneously with a distance from an edge of the first waveguide to an edge of the second waveguide being substantially equal to a diameter of the head; and
a signal analyzer connected to the first waveguide and the second waveguide, such that the signal analyzer receives a first response from the first waveguide and a second response from the second waveguide, and compares the first response with the second response to form a comparison used to determine whether the metallic structure comprises an inconsistency within 0.1 inch from the head of the fastener.

14. The apparatus of claim 13, wherein the first signal and the second signal are both polarized in a direction that is substantially perpendicular to a plane in which the inconsistency is expected to be located.

15. The apparatus of claim 13 further comprising:
a first opening comprised by the first waveguide; and
a second opening comprised by the second waveguide, wherein the first opening is offset from the second opening, each opening being offset substantially perpendicular to, and on opposite sides of, a line formed from a center point comprised by an end of the first waveguide to a center point comprised by an end of the second waveguide.

16. The apparatus of claim 13, wherein the metallic structure is a metallic skin on an aircraft.

17. The apparatus of claim 13 further comprising a signal generator configured to generate the first signal and the second signal.

18. The apparatus of claim 17, further comprising the signal generator configured to send an initial signal into a signal divider configured to divide the initial signal into the first signal and the second signal.

19. The apparatus of claim 18, further comprising the signal divider being located in one of: the signal generator, and a probe.

20. The apparatus of claim 18, wherein the signal divider is a magic tee.

* * * * *